(12) United States Patent
Ghosh

(10) Patent No.: US 9,393,075 B2
(45) Date of Patent: Jul. 19, 2016

(54) SURGICAL SYSTEM

(71) Applicant: Krishnan K. Ghosh, Chicago, IL (US)

(72) Inventor: Krishnan K. Ghosh, Chicago, IL (US)

(*) Notice: Subject to any disclaimer, the term of this patent is extended or adjusted under 35 U.S.C. 154(b) by 0 days.

(21) Appl. No.: 14/831,629

(22) Filed: Aug. 20, 2015

(65) Prior Publication Data
US 2015/0351849 A1    Dec. 10, 2015

Related U.S. Application Data

(63) Continuation of application No. 14/080,391, filed on Nov. 14, 2013, now abandoned, which is a continuation-in-part of application No. 13/678,843, filed on Nov. 16, 2012, now abandoned.

(60) Provisional application No. 61/808,837, filed on Apr. 5, 2013.

(51) Int. Cl.
*A61B 19/02* (2006.01)
*B65D 65/02* (2006.01)
(Continued)

(52) U.S. Cl.
CPC ............ *A61B 19/0271* (2013.01); *A61B 19/08* (2013.01); *A61B 19/081* (2013.01); *A61B 19/26* (2013.01); *A61B 2019/0202* (2013.01);
(Continued)

(58) Field of Classification Search
CPC .. A61B 19/02; A61B 19/026; A61B 19/0271; A61B 19/08; A61B 19/081; A61B 19/088; A61B 19/10; A61B 2019/0267; A61B 2019/0268; A61B 2019/027
USPC .............. 206/370, 524.8, 562, 563, 564, 438, 206/363, 570, 571, 572; 150/154, 158; 128/849, 852
See application file for complete search history.

(56) References Cited

U.S. PATENT DOCUMENTS

D249,774 S    10/1978  Seager
4,626,971 A * 12/1986  Schultz ............... F21V 33/0068
                                                              206/365
4,905,710 A    3/1990   Jones
(Continued)

FOREIGN PATENT DOCUMENTS

WO    WO2012151062    11/2012

OTHER PUBLICATIONS

Office Action mailed Mar. 18, 2015 in U.S. Appl. No. 13/678,843.
(Continued)

*Primary Examiner* — Steven A. Reynolds
*Assistant Examiner* — Javier A Pagan
(74) *Attorney, Agent, or Firm* — Neal, Gerber & Eisenberg LLP

(57) ABSTRACT

A surgical system is disclosed. The surgical system can include a tray and a vacuum-fitted cover covering at least a portion of the tray. The surgical system can comprise a tray and a drape at least partially vacuum-fitted to the tray. A surgical drape is also disclosed. The surgical drape can comprise a cover including an opening and an interior cavity defined by a flexible wall which is configured to receive a support surface. The surgical drape can further comprise a closable portion configured to close the opening and seal at least a portion of the support surface within the interior cavity. The surgical drape can further include a valve in fluid communication with the interior cavity, wherein the valve is configured to enable the suction of air from the interior cavity and draw the flexible wall inwardly to closely envelop at least a portion of the support surface.

29 Claims, 14 Drawing Sheets

(51) Int. Cl.
*A61B 19/08* (2006.01)
*A61B 19/00* (2006.01)

(52) U.S. Cl.
CPC ... *A61B2019/025* (2013.01); *A61B 2019/0278* (2013.01); *A61B 2019/0286* (2013.01)

(56) References Cited

U.S. PATENT DOCUMENTS

| | | | |
|---|---|---|---|
| 5,122,904 A | 6/1992 | Fujiwara et al. | |
| 5,170,804 A * | 12/1992 | Glassman | 128/849 |
| 5,362,021 A * | 11/1994 | Phillips | A61G 13/101 248/124.1 |
| 5,429,142 A | 7/1995 | Szabo et al. | |
| 5,543,832 A | 8/1996 | Oravecz et al. | |
| D381,515 S | 7/1997 | Haynes | |
| 5,765,565 A | 6/1998 | Adair | |
| 5,871,015 A * | 2/1999 | Lofgren | 128/849 |
| 5,970,980 A | 10/1999 | Adair | |
| 6,056,439 A * | 5/2000 | Graham | B65D 77/225 220/89.1 |
| 7,614,203 B2 * | 11/2009 | Oltrogge | B65D 81/2038 53/139.2 |
| 8,848,987 B2 | 9/2014 | Nolle et al. | |
| 2006/0111725 A1 | 5/2006 | Biegun | |
| 2008/0118190 A1 * | 5/2008 | Tang | B65D 81/2038 383/103 |
| 2009/0232947 A1 * | 9/2009 | Buisson | B65D 51/1644 426/118 |
| 2010/0087852 A1 | 4/2010 | Cheatham et al. | |
| 2011/0086141 A1 * | 4/2011 | Strilich | B65D 75/305 426/110 |
| 2011/0515284 | 6/2011 | Charles | |
| 2012/0012496 A1 | 1/2012 | Schorr et al. | |
| 2012/0076440 A1 * | 3/2012 | Gallagher | B65D 33/2508 383/4 |
| 2012/0204516 A1 * | 8/2012 | Palumbo | B65B 31/028 53/403 |
| 2012/0325704 A1 * | 12/2012 | Kerns | A61B 19/0271 206/370 |
| 2013/0009606 A1 | 1/2013 | Smith et al. | |
| 2014/0138269 A1 | 5/2014 | Ghosh | |

OTHER PUBLICATIONS

International Preliminary Report on Patentability dated May 28, 2015 in International Application No. PCT/US2013/070127.
Office Action mailed Dec. 22, 2014 in U.S. Appl. No. 14/080,391.
Office Action mailed Jun. 9, 2015 in U.S. Appl. No. 13/678,843.
Office Action mailed Sep. 4, 2014 in U.S. Appl. No. 13/678,843.
Search Report and Written Opinion dated Apr. 9, 2014 in International Application No. PCT/US2013/070127.
Office Action mailed Apr. 1, 2015 in U.S. Appl. No. 14/080,391.

* cited by examiner

SURGICAL SYSTEM

CROSS-REFERENCE TO RELATED APPLICATIONS

The present application is a continuation application of U.S. patent application Ser. No. 14/080,391, filed on Nov. 14, 2013, which is a continuation-in-part application under 35 U.S.C. §120 of U.S. patent application Ser. No. 13/678,843, filed on Nov. 16, 2012; U.S. patent application Ser. No. 14/080,391, filed on Nov. 14, 2013, also claims the benefit under 35 U.S.C. §119(e) of and priority to U.S. Provisional Patent Application Ser. No. 61/808,837, filed on Apr. 5, 2013, the entire disclosure each of which is incorporated by reference herein.

FIELD OF THE INVENTION

The present invention relates to surgical systems for at least partially covering an object in an operating room, for instance. In various instances, the surgical system can include a tray and a vacuum-fitted cover covering at least a portion of the tray. In certain instances, the surgical system can include a tray and a drape at least partially vacuum-fitted to the tray. The present invention also relates to methods for using the surgical systems disclosed herein.

BACKGROUND OF THE INVENTION

A conventional operating room setup typically includes various fixtures including a back table. A back table is often a sterilized table which is used to hold instrumentation needed during a surgical procedure. In order to maintain a sterile environment, the table is usually sterilized, covered, and/or disposable. It is typically located laterally with respect to and separately from the patient operating bed. As a result of this arrangement, it can be inconvenient for a surgeon to move between the patient bed and the back table. Furthermore, items may be dropped and/or otherwise compromised when they are being moved between the back table and the patient bed.

Typical back tables may also require various items and configurations which are selected based on the procedure being performed and/or the preferences of the surgeon. Often, a bowl with sterile fluid is used during a procedure and is placed on the back table. This bowl typically must be disposed of after use, and can be susceptible to spilling. Mayo Stand type tables have been proposed for use to allow a tray to overhang a bed; however, various limitations often make the use of such devices inconvenient, as described below.

A number of conventional back tables or stands have been proposed and used in the industry; however, they lack various helpful configurations. For example, U.S. Pat. No. 3,738,405, entitled MAYO STAND COVER, issued to Ericson, the entire disclosure of which is incorporated by reference herein, discloses a Mayo Stand with a cover. The stand can be moved over a bed; however, its configuration results in a very limited range of positioning options. More specifically, the stand can block light and be in the way of the surgeon if it were used over an operating bed. Moreover, any containers or bowls positioned thereon may be loosely placed on the stand and may be susceptible to being spilled.

U.S. Pat. No. 5,170,804, entitled MAYO-STAND DISPOSABLE DRAPE, issued to Glassman, the entire disclosure of which is incorporated by reference herein, discloses a Mayo Stand with a disposable drape. The drape can hold a kit of instruments which can be laid out on the stand. However, the same limitations with positioning, blocking light, and obstructing access to the patient apply to this design as well.

Another Mayo Stand cover is disclosed by U.S. Pat. No. 5,411,036, entitled MAYO STAND COVER, issued to Wilkes, the entire disclosure of which is incorporated by reference herein. Configurations such as these address the issue of covering the stand; however, the cover is inconvenient to apply, and it does not address the various issues raised above. The various conventional cover or drape systems give rise to numerous problems, including drapes not conforming closely to the underlying tables, and having the risk of sliding off of surfaces, which can compromise sterility of surfaces and supplies.

Another Mayo Stand cover is disclosed in U.S. Pat. No. 5,871,015, entitled MAYO STAND COVER, issued to Lofgren et al., and a further surgical table cover is disclosed in U.S. Pat. No. 7,104,201, entitled STERILE SURGICAL TABLE COVER, issued to Comeaux et al., the entire disclosures of which are incorporated by reference herein. Other cover systems and Mayo Stands exist; however, none of these devices overcome the problems of bowls being spilled, requiring bowls to be disposed of, limitations in range of positioning, light blockage, etc.

In U.S. Pat. No. 6,142,152, entitled COVER FOR AN OPERATING ROOM BACK TABLE, issued to Gawarecki, the entire disclosure of which is incorporated by reference herein, a cover for an operating room back table is disclosed. This cover is unwrapped to supply a kit of supplies and cover the stand. An air permeable section of the cover helps enable the cover to be unwrapped quickly. The same limitations as discussed above apply.

Surgeons often find it convenient to have compartments available where items can be placed or stored during a procedure. U.S. Pat. No. 6,874,505, entitled SURGICAL DRAPE SYSTEM WITH POUCH, issued to Fenwick et al., the entire disclosure of which is incorporated by reference herein, discloses a surgical drape system which covers the patient. The drape includes a pouch which can be accessed during the procedure. However, this is highly inconvenient for a number of procedures as portions of the patient's body may be blocked from access. Furthermore, this drape clearly does not replace the need for a tray or table top for further supplies.

Various drape covers exist; however, they either involve loosely placing a drape over the top of a surface, or covering the object similar to a pillow case, however, there is no close conformity to the surface of the object, which can cause problems in certain instances. Furthermore, disposing of such drapes after use can be messy and cumbersome, and may require additional bags or containers. Thus, a need for an improved surgical system exists.

The foregoing discussion is intended only to illustrate various aspects of the related art in the field of the invention at the time, and should not be taken as a disavowal of claim scope.

The features and advantages of this invention, and the manner of attaining them, will become more apparent and the invention itself will be better understood by reference to the following description of embodiments of the invention taken in conjunction with the accompanying drawings, wherein.

DETAILED DESCRIPTION

Figure 1:
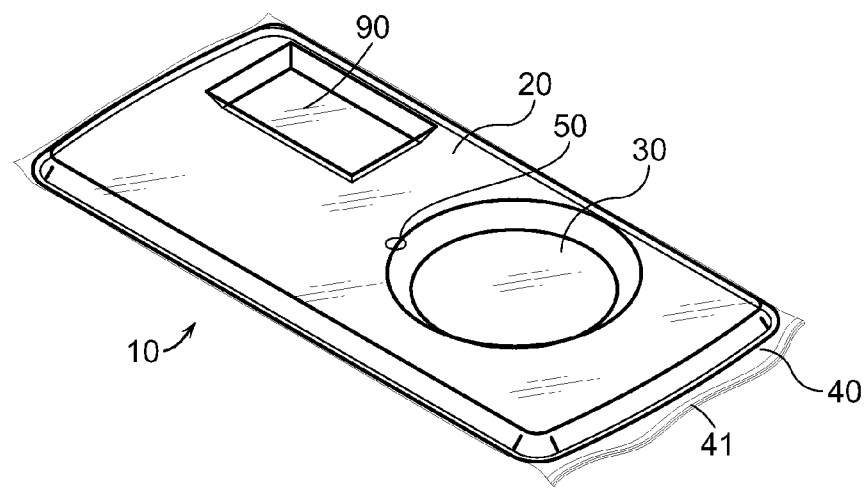
FIG. 1 is a perspective view of a surgical tray system in accordance with at least one embodiment.
Figure 2:
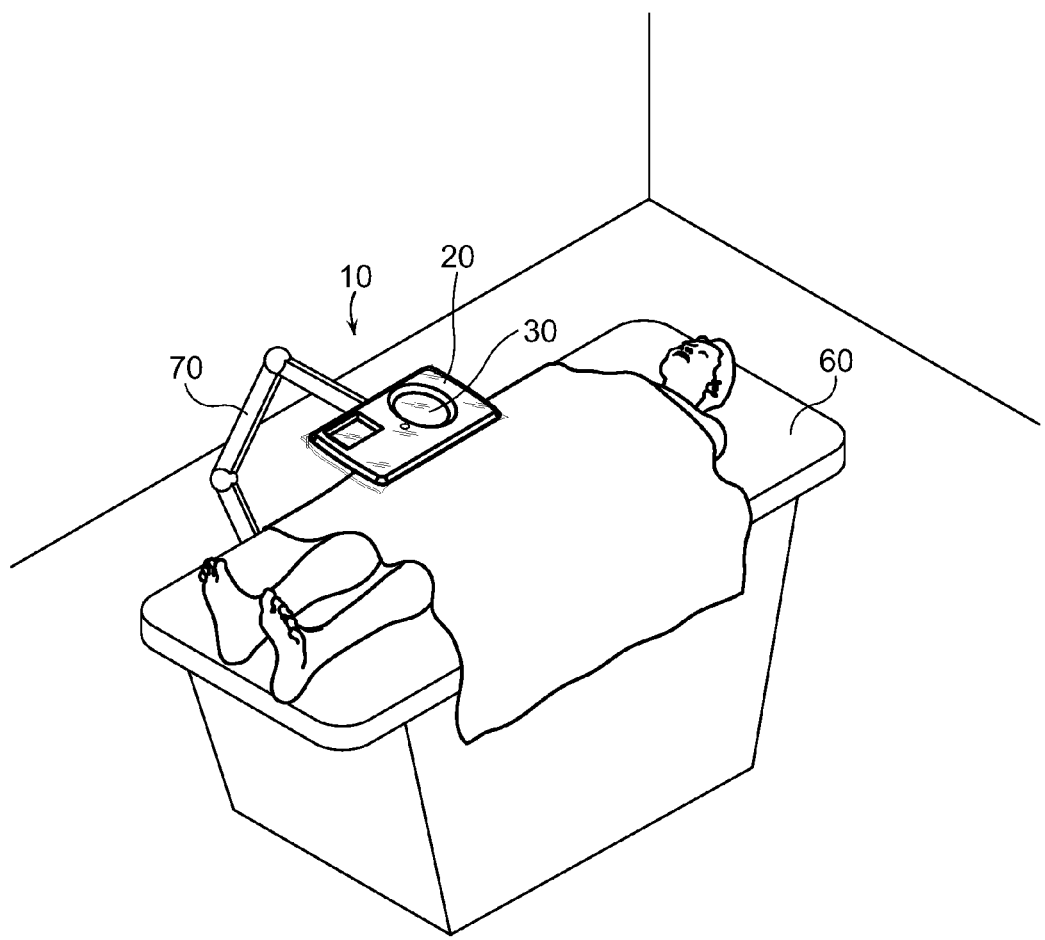
FIG. 2 is a perspective view of the surgical tray system of FIG. 1 positioned over a patient in accordance with at least one embodiment.

A surgical tray system 10 is illustrated in FIG. 1. Among other things, the system 10 includes a tray 20. The tray 20 can have any suitable shape. In various instances, the tray 20 can be substantially planar, for example. In certain instances, the tray 20 can include an upper surface and a lower surface, for example. For the purposes of at least this embodiment, referring generally to FIG. 2, the lower surface of the tray 20 can comprise a surface that faces toward a patient while the upper surface of the tray 20 can comprise a surface that faces away from the patient. The tray 20 can further comprise one or more indentations, such as indentation 30, for example, defined therein. In various instances, the indentation 30 may be bowl-shaped. A bowl-shaped indentation 30 can include a recess defined in the upper surface of the tray 20 and/or protrusion extending downwardly from the lower surface of the tray 20, for example. The indentation 30 can comprise a container, such as open-sided container, for instance, configured to receive and support a surgical instrument therein, for instance.

Figure 9:
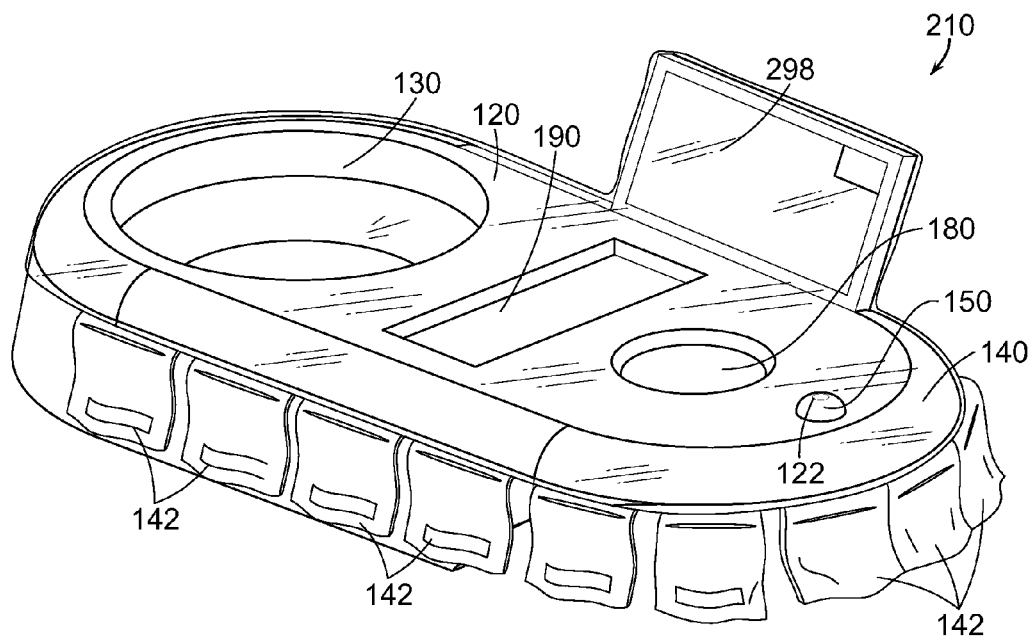
FIG. 9 is a perspective view of another surgical tray system in accordance with at least one embodiment.

The tray 20 can comprise at least one aperture defined therein. Such an aperture can permit a clinician to observe a patient, or a surgical site in the patient, through the tray 20. In various instances, the aperture can comprise a through-hole extending between the upper surface and the lower surface of the tray 20. In various instances, the tray 20 can comprise at least one window. A window can include a clear, transparent, substantially clear, substantially transparent, and/or translucent material, such as glass and/or polycarbonate, for example, which can be positioned within an aperture defined in the tray 20. Such a window can permit a clinician to observe a patient, or a surgical site in the patient, through the tray 20. In various instances, the window can be integrally formed with the tray. In certain instances, the window can be removably assembled to the tray. In certain instances, the tray 20 can include at least one magnification element, such as magnification element 90, for example. Such a magnification element can magnify an area below the lower surface of the tray 20 when viewed from above the tray 20 and permit a clinician to more easily observe a patient, or a surgical site in the patient, through the tray 20. In various instances, the magnification element can comprise a lens, for example. In some instances, the tray 20 can include a camera, such as a digital camera, for example, and/or an electronic display, such as a video screen, for example, configured to display a magnified image. A video screen 298 of a surgical tray system 210 is depicted in FIG. 9. In various instances, referring again to FIG. 1, the tray 20 can include a plurality of cameras and/or a plurality of electronic displays. In such instances, the tray 20 can include one or more power sources, such as a battery, for example, which can be configured to supply power to the camera(s) and/or monitor(s). In any event, a magnification element can be integrally formed with the tray 20. In certain instances, a magnification element can be removably assembled to the tray 20.

Further to the above, the tray system 10 can include a magnification element 96. Magnification element 96 can extend from an edge of the tray 20, for instance, and, similar to the above, magnification element 96 can be positioned and adapted to magnify an area below the lower surface of the tray 20 when viewed from above the tray 20. Various other magnification elements are also contemplated. In various instances, a cover positioned over and/or surrounding the tray 20 can include at least one magnification element. For example, a magnification element 92 may be integral with and/or attached to a drape 40, for example. In certain instances, the drape 40 can include a magnification element, such as a flap 94, for example, which can comprise an extension of the drape 40. The flap 94 may either be integral with the drape 40 and/or removably affixed to the drape 40, for example. In various instances, the drape 40 can include one or more cameras attached thereto. In certain circumstances, the drape 40 can include one or more power sources and/or one or more wireless transmitters which can permit the camera(s) to communicate wirelessly with the electronic display(s) in the tray 20, discussed above, for example.

The tray 20 can be comprised of any suitable material. For instance, the tray 20 can be comprised of resin, plastic, fiber re-enforced plastic, a carbon fiber material, aluminum, and/or stainless steel, for example. In various instances, the tray 20 can be at least partially comprised of a clear, transparent, substantially clear, substantially transparent, and/or translucent material, such as glass and/or polycarbonate, for example. In certain instances, the tray 20 can be entirely comprised of a clear, transparent, substantially clear, substantially transparent, and/or translucent material, such as glass and/or polycarbonate, for example. Such materials can permit a clinician to observe a patient, or a surgical site in the patient, through the tray 20, for instance. Moreover, such materials can permit light to pass through the tray 20. In certain circumstances, light can pass through the tray 20 and illuminate the patient and/or the surgical site in the patient, for example.

In various embodiments, the tray system 10 may also include at least one light source, such as light source 80, for example. The light source 80 can comprise any suitable light source, such as an incandescent bulb and/or a light emitting diode (LED), for example. The light source 80 can be mounted to the tray 20 and, in various instances, the light source 80 can be adapted and positioned to illuminate an area beneath the tray 20. In certain instances, the light source 80 can be fixedly mounted to the tray 20. In some instances, the light source 80 can be removably mounted to the tray 20. In various instances, the light source 80 can be mounted relative to and/or onto the lower surface of the tray 20. In certain instances, the light source 80 can be configured to project light from the lower surface of the tray 20. The light source 80 may also be adjustable. For instance, the intensity of the light source 80 may be adjustable and/or the orientation of the light source 80 may be adjustable. In such instances, a clinician can be configured to control the amount of light that the light source 80 projects onto a desired area. The tray system 10 can further comprise at least one battery, for example, and/or any other suitable power source configured to supply power to the light source 80. In various instances, the drape 40, for instance, can include at least one light source. In certain instances, the drape 40 can include at least one power source, such as a battery, for example.

In various instances, the tray 20 can be comprised of a single, unitary piece of material. In other instances, the tray 20 can be comprised of a plurality of portions which have been assembled together. In at least one such instance, the tray 20 can be comprised of modular portions which have been assembled together. In certain instances, the tray 20 can be comprised of a first modular portion and a second modular portion which have been selected from three or more modular portions. The modular portions of the tray 20 can include interlocking connectors, for instance, which can secure the modular portions together. In various instances, the modular portions of the tray 20 can be secured together utilizing one or more fasteners, for example.

Referring again to FIG. 1, the surgical tray system 10 can further include a cover, such as drape 40, for example. In various instances, the drape 40 can comprise a bag. In certain instances, the drape 40 can comprise a flexible wall which defines an interior cavity and an opening. The opening can be sized and configured to permit at least a portion of the tray 20 to be positioned within the interior cavity. In various instances, the interior cavity can be sized and configured to receive the entirety of tray 20. In certain instances, a cover can include a plurality of interior cavities and one or more openings in communication with each interior cavity. In any event, the drape 40 can further comprise at least one sealing element which can be configured to close the opening and seal, or at least substantially seal, the tray 20 in the interior cavity of the drape 40. For instance, the drape 40 can include a closable end and a sealing element 41 which can be configured to close and seal the closable end. For the purposes of at least this embodiment, and/or any other suitable embodiment, the drape 40 can be substantially sealed if a vacuum can be induced within the interior cavity. In such instances, as described in greater detail below, the vacuum created within the interior cavity can draw the flexible wall of the drape 40 inwardly to vacuum fit the drape 40 around the tray 20. The vacuum created within the interior cavity need not be an absolute vacuum; in fact, the vacuum can have a vacuum pressure which is less than the pressure of the atmosphere surrounding the drape 40. In various instances, the sealing element 41 can comprise any suitable sealing element such as, for example, a tongue and groove system, a draw string, an adhesive strip such as with a pull away adhesive cover, a clamp, a plurality of clamps, and/or any other suitable means.

Figure 24:
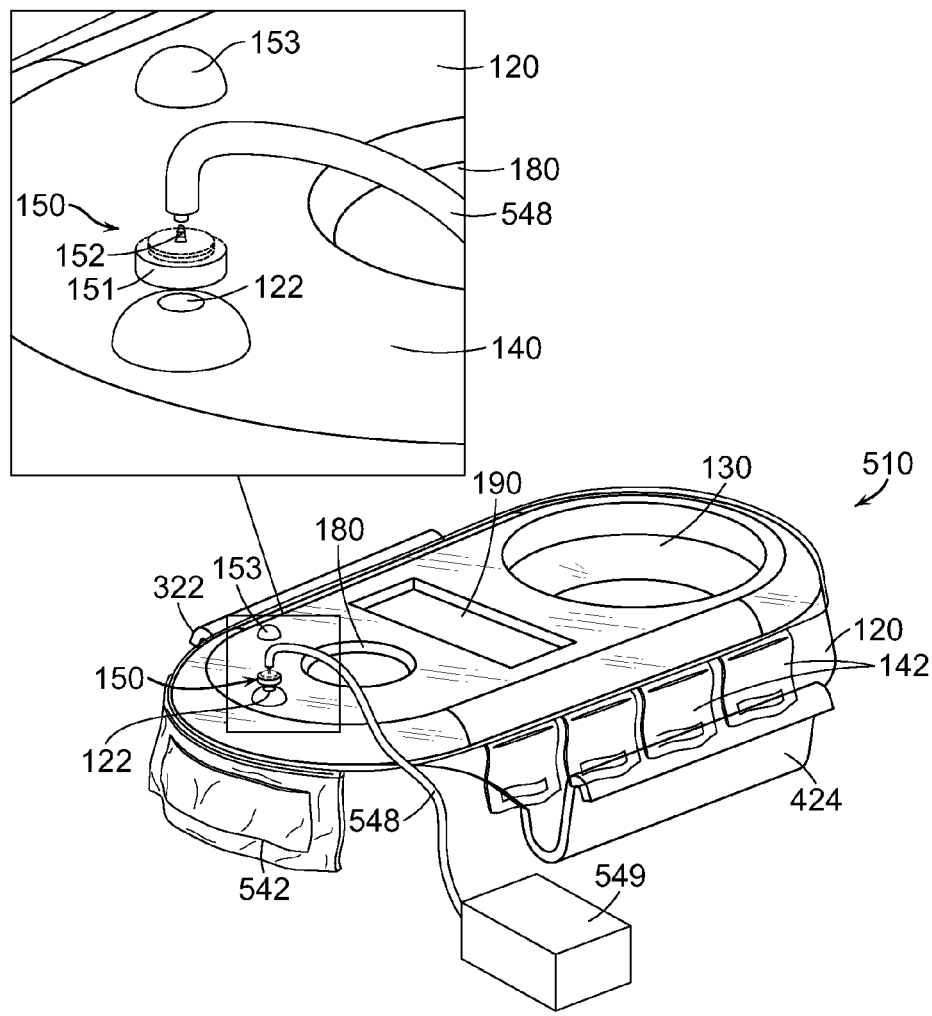
FIG. 24 is a perspective view illustrating a vacuum source being attached to a valve of the surgical drape of FIG. 23.
Figure 25:
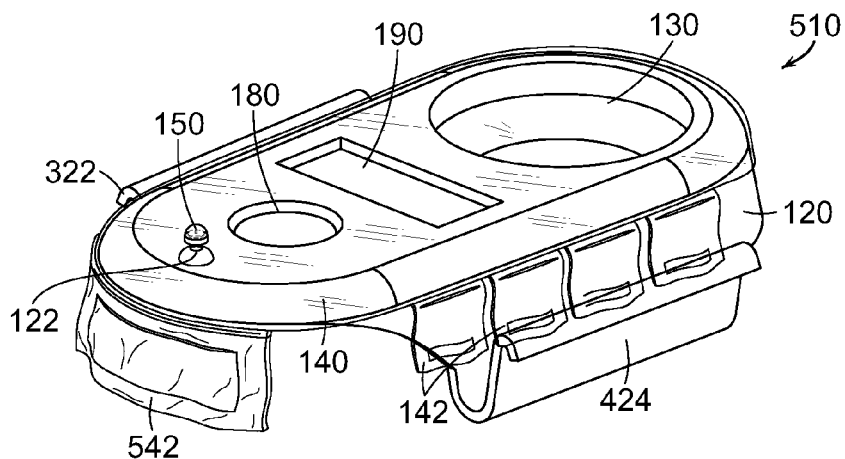
FIG. 25 is a perspective view of the surgical drape of FIG. 23 vacuum-fitted to the tray of FIG. 22.
Figure 26:
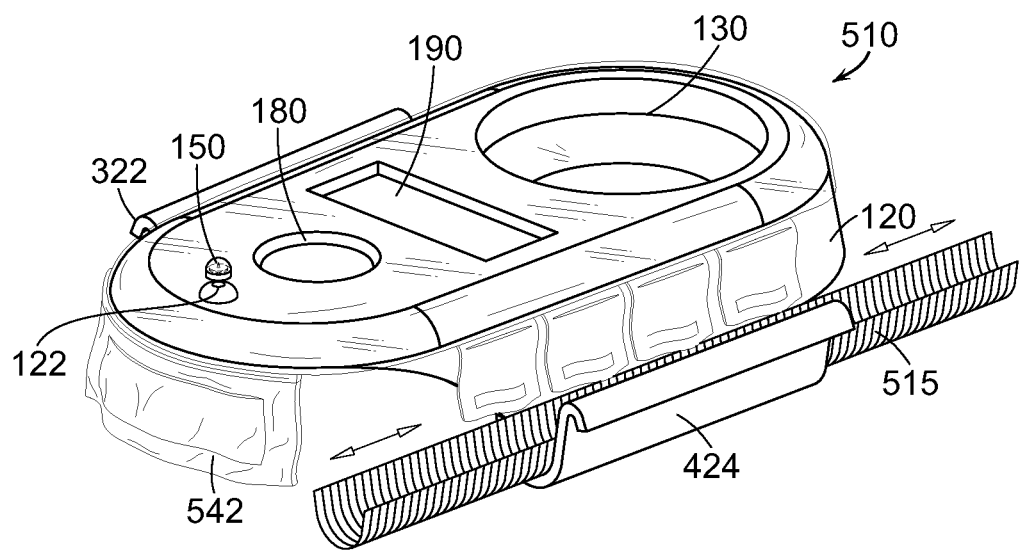
FIG. 26 is a perspective view of a modular channel assembled to the tray of FIG. 22.
Figure 27:
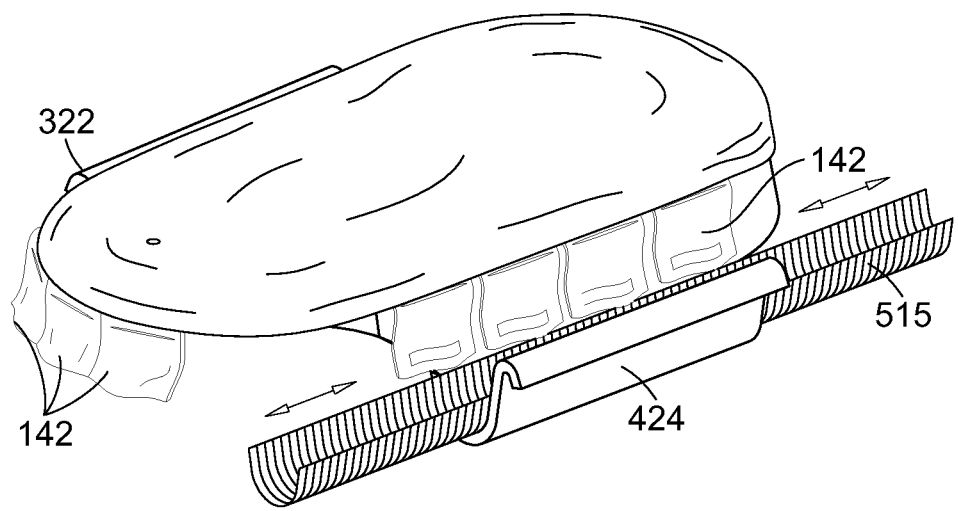
FIG. 27 is a perspective view of a surgical tray system in accordance with at least one embodiment.

Referring again to FIG. 1, the drape 40 can include at least one valve, such as valve 50, for example, which can be in fluid communication with the interior cavity of the drape 40. Further to the above, the valve 50 can be utilized to generate a vacuum within the interior cavity. In various instances, the valve 50 can comprise a one-way valve and can comprise a first port and a second port. The first port can be configured such that a vacuum source can be attached to and/or sealed to the valve 50 while the second port can be in communication with the interior cavity. A vacuum source 549 and a vacuum conduit 548 are depicted in FIG. 24. The one-way valve can permit the flow of air from the second port toward the first port when the vacuum is applied to the first port. When the vacuum is not being applied to the first port, the one-way valve can prohibit the flow of air between the first port and the second port, thereby creating a seal within the valve 50. In certain instances, the valve 50 can comprise a two-way valve and can comprise a first port and a second port. The first port of the two-way valve can be configured such that a vacuum source can be attached to and/or sealed to the valve 50 while the second port can be in communication with the interior cavity. The two-way valve can permit the flow of air from the second port toward the first port when the vacuum is applied to the first port. The two-way valve can also permit the flow of air from the first port toward the second port when the vacuum is applied to the second port. As will be described in greater detail below, this particular function of the two-way valve may be useful when the drape 40 has been inverted during a disposal process, for example. When the vacuum is not being applied to the first port or the second port, the two-way valve can prohibit the flow of air between the first port and the second port, thereby creating a seal within the valve 50. In various instances, any suitable valve can be utilized.

Figure 8:
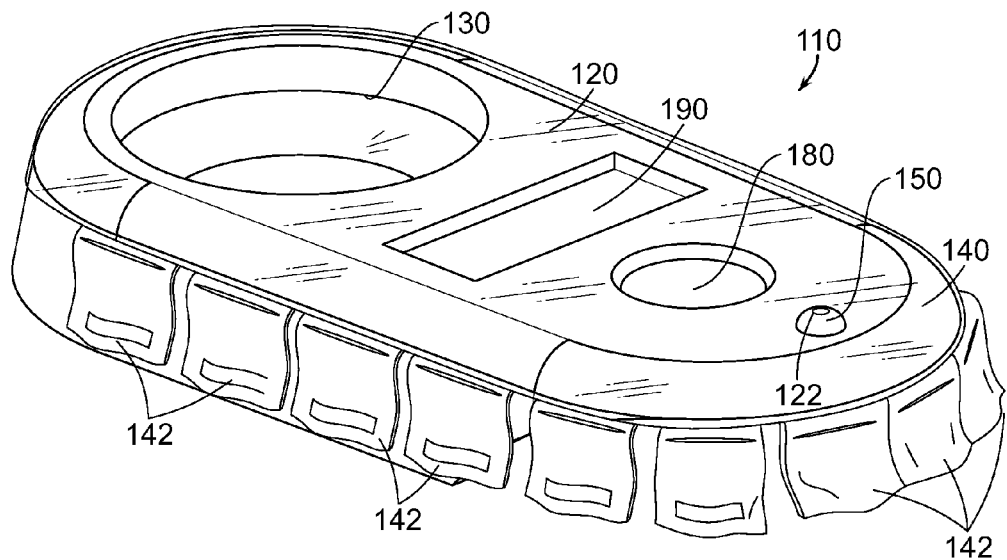
FIG. 8 is a perspective view of another surgical tray system in accordance with at least one embodiment.

As discussed above, the valve 50 can be utilized to draw the drape 40 inwardly around the tray 20. In various instances, the drape 40 can be vacuum-fitted around the tray 20 such that the drape 40 closely fits around the surface of the tray 20. In certain instances, the drape 40 can be form-fitted into the indentation 30 of the tray 20, for example. In various instances, the tray 20 can include one or more through-holes, for example, configured to permit air to flow through the tray 20 toward the valve 50 when a vacuum is created within the interior cavity of the drape 40. Turning now to FIG. 8, a surgical tray system 110 is disclosed which includes a tray 120 and a drape 140. The tray 120 and the drape 140 can be similar to the tray 20 and the drape 40 in many respects. For instance, the drape 140 can include a valve 150 and the tray 120 can include a bowl-shaped indentation 130, a light 180, and a magnification element 190, for example. The tray 120 can also include an air flow aperture, or vent, 122 in fluid communication between the upper side and the lower side of the tray 120. In various instances, the air flow aperture 122 can be aligned, or at least substantially aligned, with the valve 150. In many instances, as a result of the above, air pockets within the drape 40 can be reduced and/or eliminated.

As the reader will appreciate, the drape 40 and/or the drape 140 can be sufficiently flexible such that it conform, or at least substantially conform, around the tray 20 and/or the tray 120, for example. In some circumstances, the drape 40 and/or the drape 140 can be comprised of a thin-wall material, for example. A thin-wall material can comprise any suitable material which can deflect inwardly toward the tray, for example. The drape 40 and/or the drape 140 may be formed of any suitable material, including but not limited to woven material, non-woven material, plastic, latex, and/or latex-free material, for example. In various instances, the drape 40 and/or the drape 140 can be comprised of, or at least partially comprised of, a clear, transparent, substantially clear, substantially transparent, and/or translucent material, for example. Such embodiments can be especially useful in combination with embodiments including a tray which is comprised of, or at least partially comprised of, a clear, transparent, substantially clear, substantially transparent, and/or translucent material, for example. Such embodiments can permit a clinician to view an area below the lower surface of the tray when viewed from above the tray and permit a clinician to more easily observe a patient, or a surgical site in the patient, through the tray and the drape.

Figure 3:
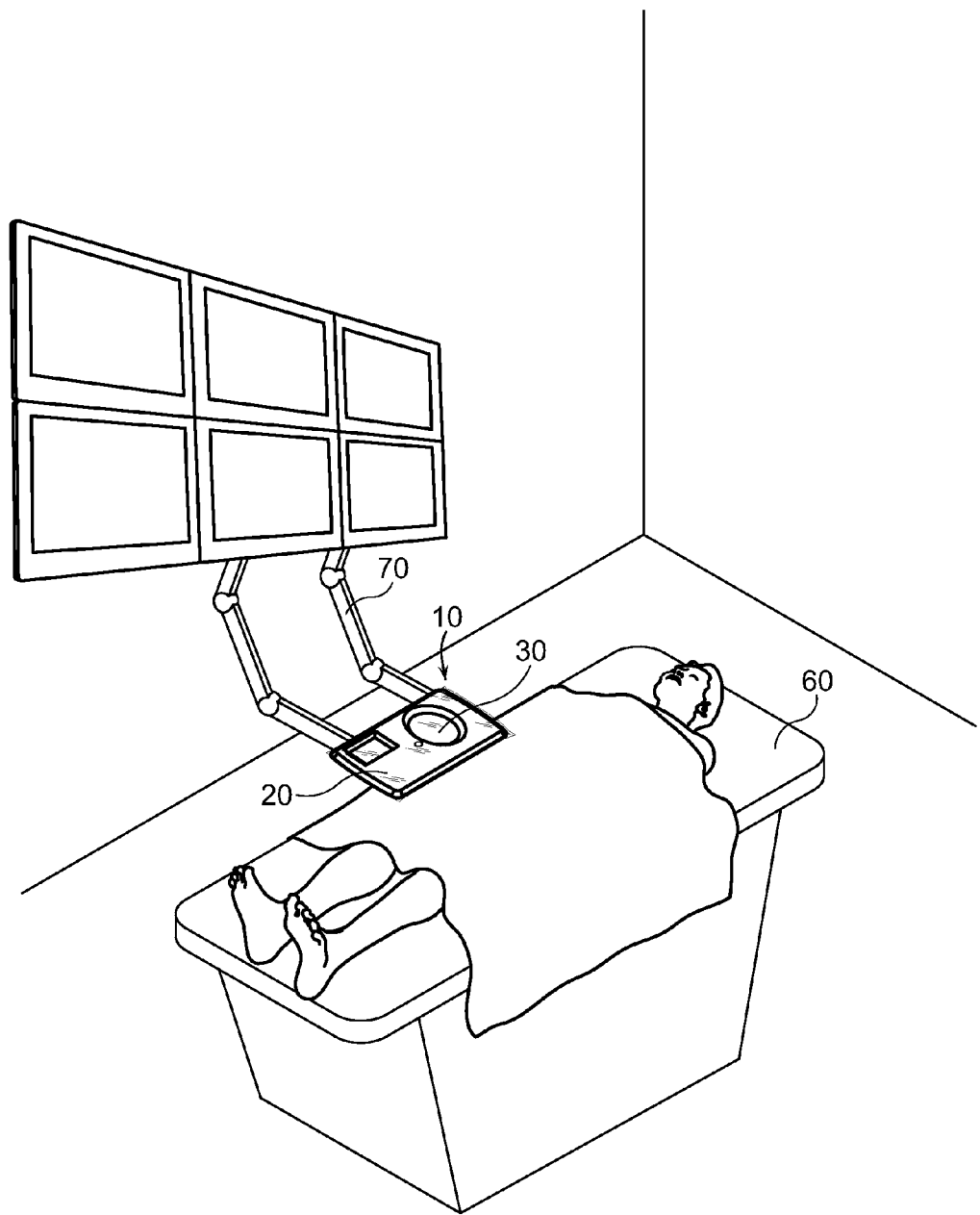
FIG. 3 is a perspective view of the surgical tray system of FIG. 1 positioned over a patient in accordance with at least one embodiment.
Figure 4:
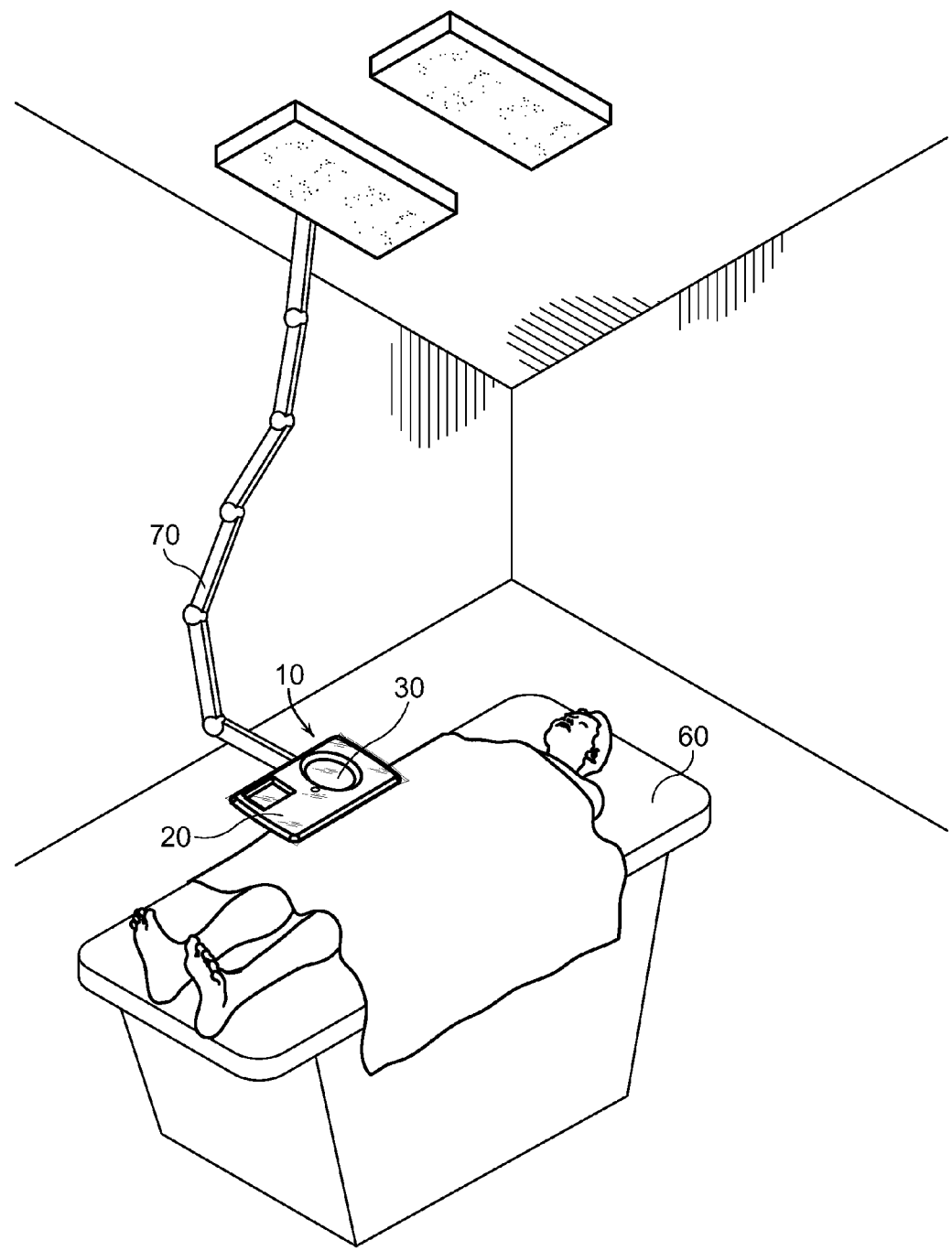
FIG. 4 is a perspective view of the surgical tray system of FIG. 1 positioned over a patient in accordance with at least one embodiment.

As the reader will appreciate from the above, a cover can be vacuum-fitted, or at least substantially vacuum-fitted, around a surgical tray. In various instances, as outlined above, the tray 20 can be completely encapsulated by the drape 40, as depicted in FIG. 1. In certain instances, referring to FIG. 2, the tray 20 can be supported by an arm 70 which can permit the surgical tray system 10 to be movably mounted above a patient bed 60, for example. In certain circumstances, the tray 20 may be mounted to an arm 70 which is attached to a bed frame member. In various instances, arm 70 can comprise one or more articulation joints that can be configured to allow a range of positioning options for the tray system 10. In certain instances, as a result, the tray 20 can be moved side to side, front to back, and up and down. In various instances, a travel limiting safety feature can be included to prevent the tray 20 from moving too far down toward the patient. In certain embodiments, referring to FIG. 3, an arm 70 may mount the tray system 10 to a monitor system such as those typically used in an operating room. In certain embodiments, referring to FIG. 4, an arm 70 may mount the tray system 10 to a ceiling fixture. In various embodiments, the tray system 10 could be mounted to the arm of a da Vinci surgical robot manufactured by Intuitive Surgical, Inc., for example. In any event, an arm 70 would allow the tray 20 to be positioned in a range of suitable positions.

In various circumstances, further to the above, a tray may include at least one mounting portion which can be attached to the arm 70, for example. In certain instances, the mounting portion may extend from the drape 40 and/or the arm 70 may extend into the drape 40, for example. In such circumstances, a seal can be created between the drape 40 and the tray mounting portion and/or the arm 70. Various suitable sealing elements may be used. For example, the end portion of the drape 40 may include separated tapered portions which may be sealed against the arm, such as by an adhesive, a drawstring, elastic, a clamp, a plurality of clamp elements, and/or any other suitable component or set of components. In certain embodiments, clamp sections may serve a dual purpose in that they may be used to package a kit including the drape 10.

Figure 10:
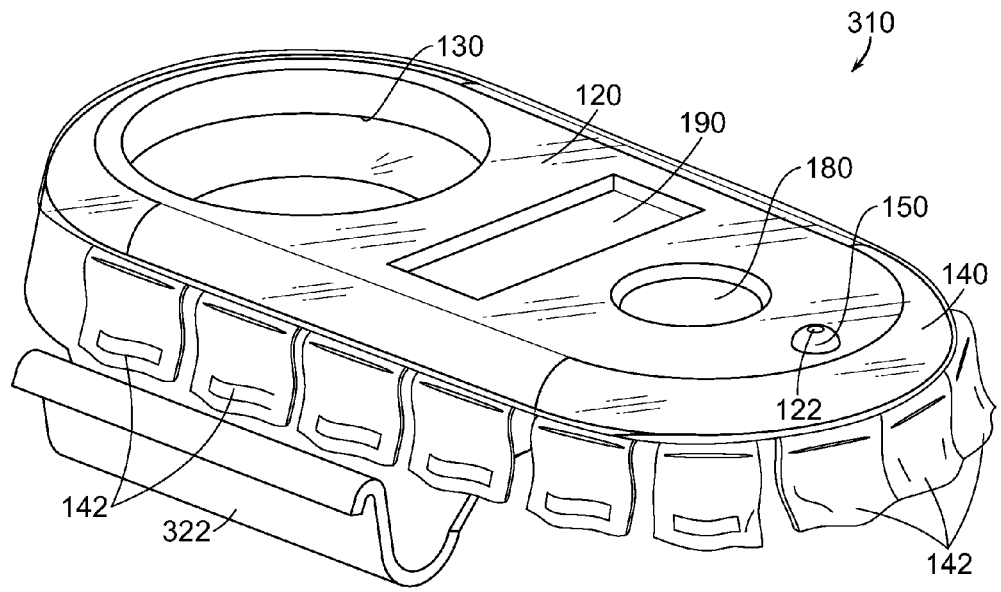
FIG. 10 is a perspective view of another surgical tray system in accordance with at least one embodiment.
Figure 11:
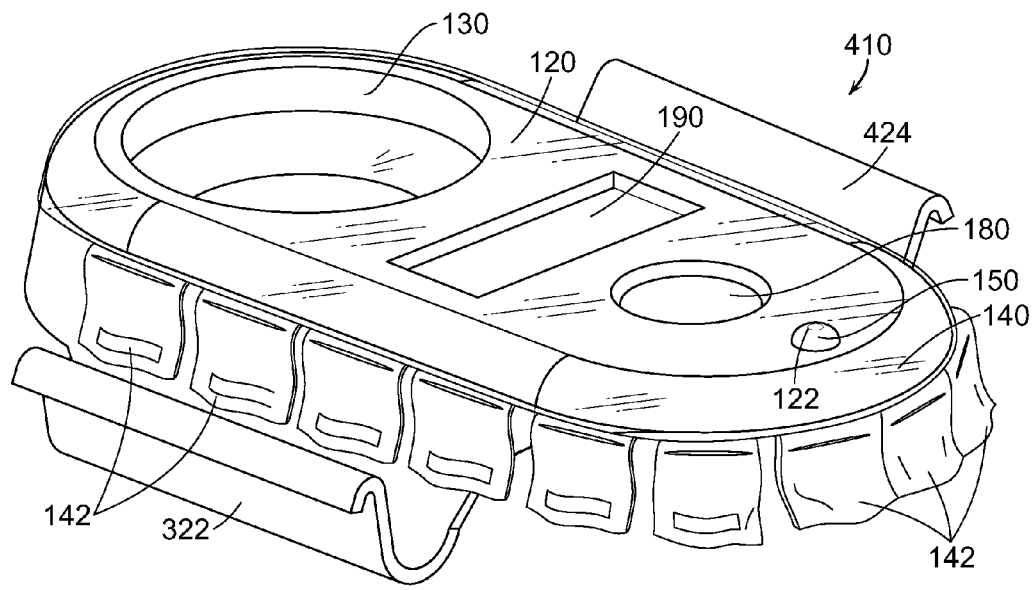
FIG. 11 is a perspective view of another surgical tray system in accordance with at least one embodiment.
Figure 18:
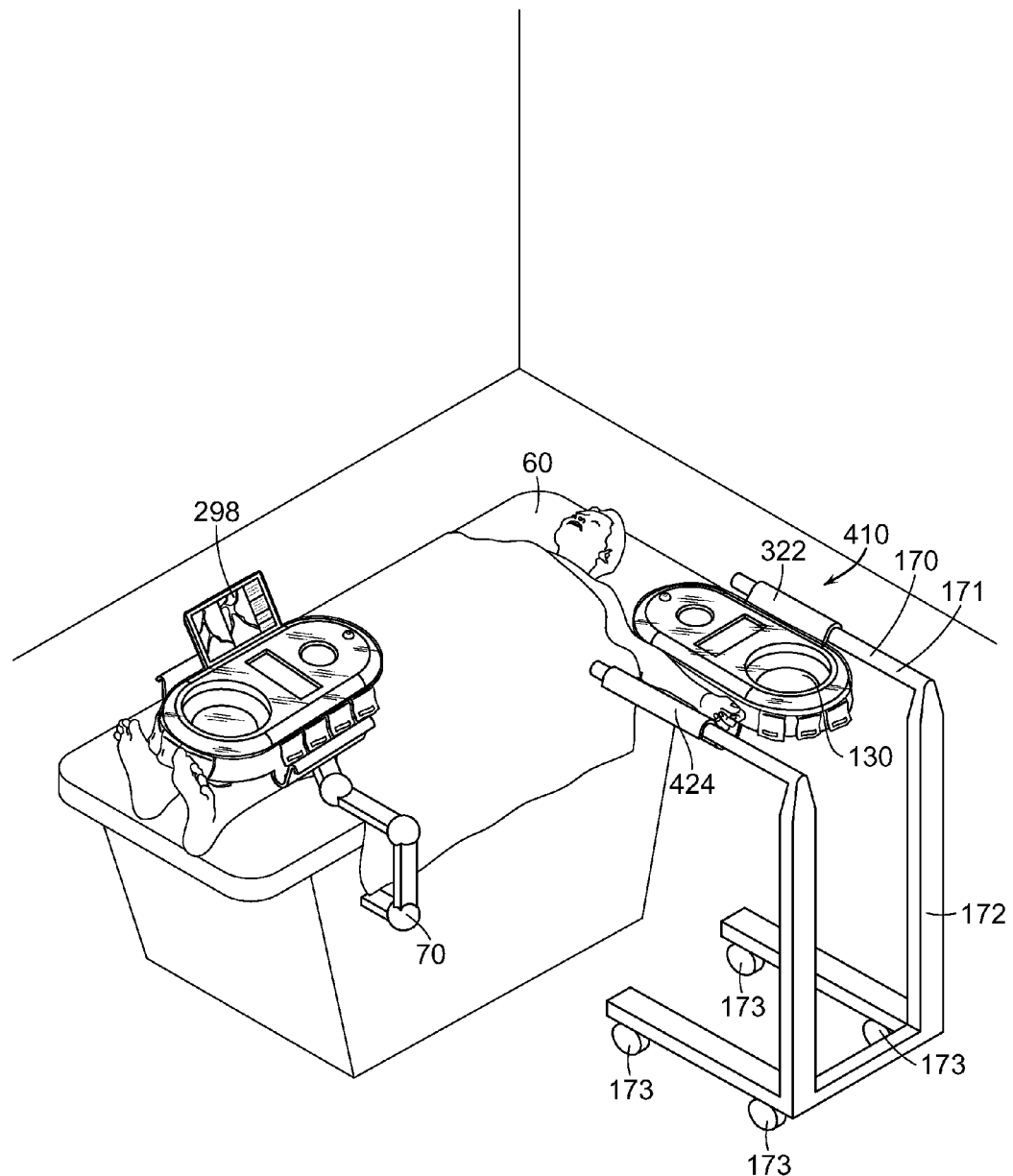
FIG. 18 is a perspective view of several surgical tray systems being utilized in an operating room.
Figure 19:
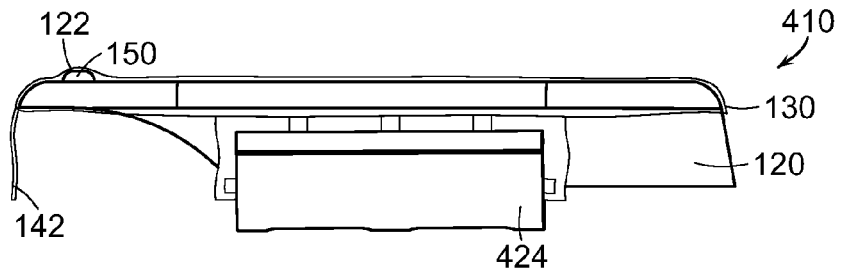
FIG. 19 is an elevational view of the surgical tray system of FIG. 11.
Figure 20:
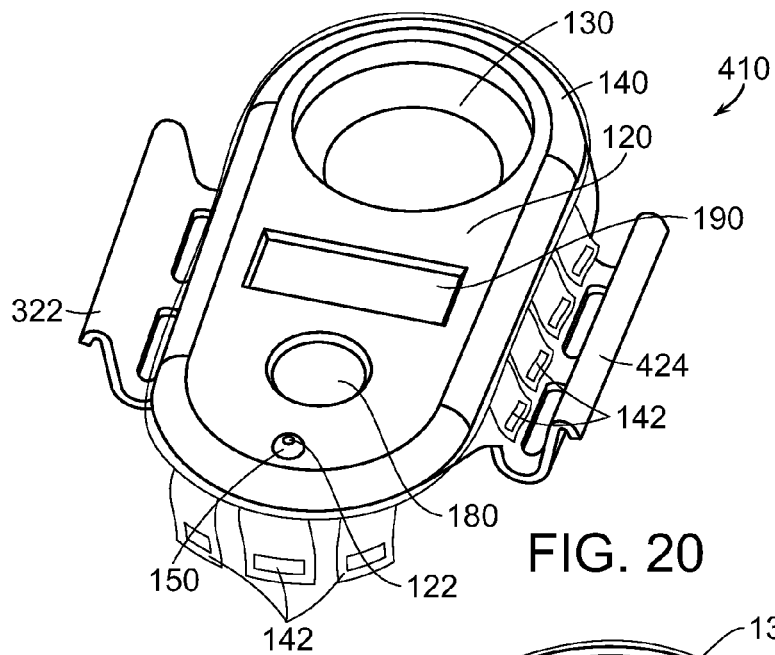
FIG. 20 is a top perspective view of the surgical tray system of FIG. 11.
Figure 21:
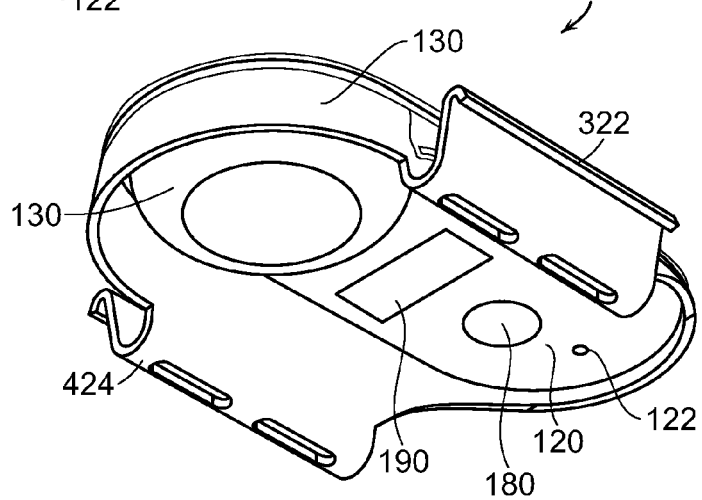
FIG. 21 is a bottom perspective view of the surgical tray system of FIG. 11.
Figure 22:
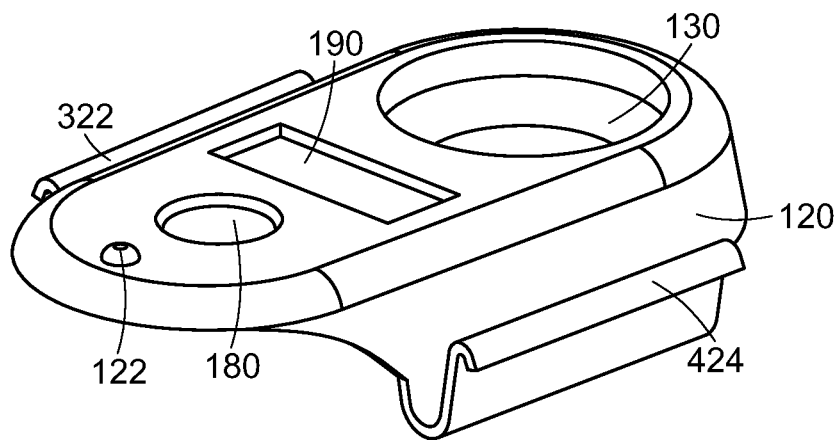
FIG. 22 is a perspective view of the tray of the surgical tray system of FIG. 11.
Figure 23:
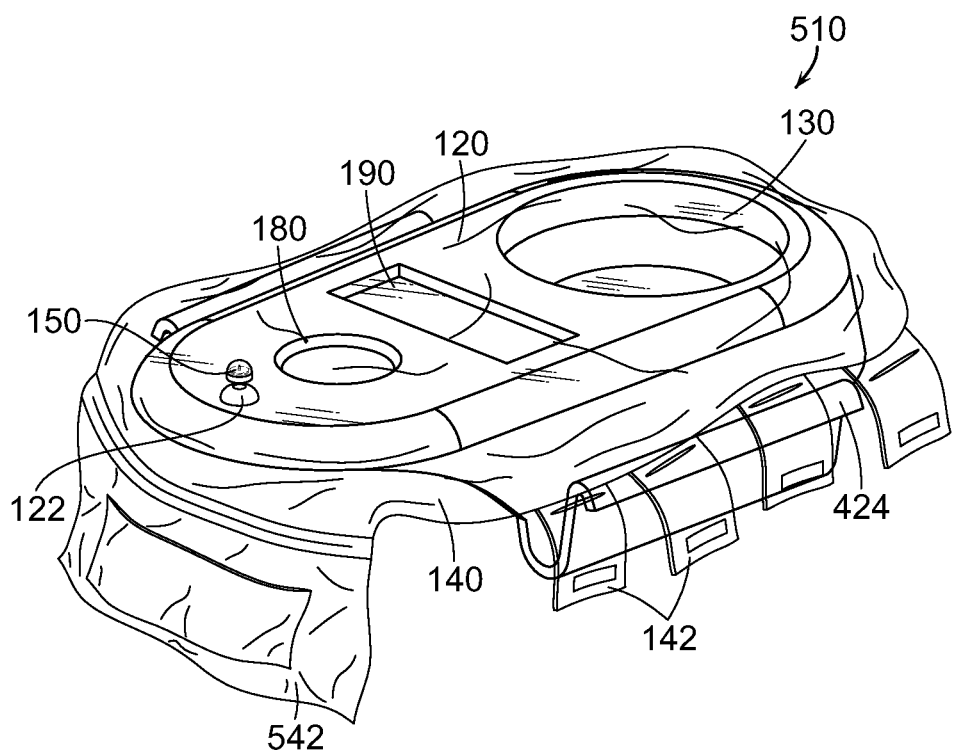
FIG. 23 is a perspective view of a surgical drape covering the tray of FIG. 22.

In certain embodiments, referring to FIG. 18, a surgical tray system can be supported by a floor-supported stand 170, for example. The stand 170 can include a frame 172 and one or more support arms 171 extending therefrom. In various instances, the surgical tray system can include one or more supports extending from the tray 120, for example. A surgical tray system 310 is depicted in FIG. 10 which includes a first support 322 extending from tray 120 while a surgical tray system 410 is depicted in FIG. 11 which includes a first support 322 and a second support 424, for example. Referring again to FIG. 18, the first support 322 of the surgical tray system 410 can be supported by a first support arm 171 while the second support 424 can be supported by a second support arm 171. As the reader will appreciate from FIG. 18, the first support 322 and/or the second support 424 can include a trough configured to receive one or more instruments therein and/or configured to support the anatomy of a patient, for example. As the reader will further appreciate, the stand 170 can include one or more wheels, such as casters 173, for example, which can facilitate the movement and positioning of the stand 170.

Figure 7:
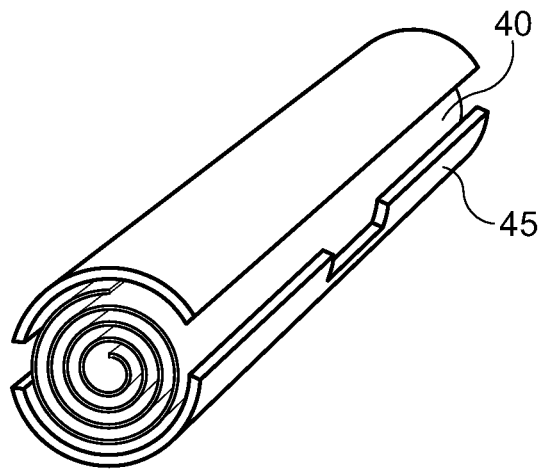
FIG. 7 is a perspective view of a container for receiving portions of a surgical tray system in accordance with at least one embodiment.

In various instances, a cover, or drape, may be vacuum-fitted around only a portion of a tray. Referring to FIG. 8, the drape 140 can comprise such a drape, for instance. In at least one such circumstance, the drape 140 may surround and cover the upper surface of the tray 120 and may grip the tray 120 when the drape 140 is vacuum-fitted around the tray 120 such that the drape 140 is held in place. While a cover, or drape, can be utilized to at least partially cover a tray, it is contemplated that a cover, such as a drape, for example, can be vacuum-fitted, or at least substantially vacuum-fitted around any suitable object in an operating room, for example. For instance, a surgical drape could be vacuum-fitted around a table, or at least a portion of a table. It is also contemplated that a surgical drape could be vacuum-fitted around a monitor, or at least a portion of a monitor, for example. In various circumstances, the cover, or drape, can be removed from the object by opening the drape and then pulling the drape off of the object. Once removed from the object, the drape can then be discarded, for example. In various instances, referring now to FIG. 7, the drape 40, for example, may be stored in a sterilized package, such as an outer sleeve or bag, and rolled up and placed in a shell 45 after it has been used. In some circumstances, the drape 40 can be delivered to the operating room in the shell 45. In certain circumstances, the shell 45, or a portion thereof, can be configured to provide a useful channel. For instance, the shell 45 can be placed on a patient bed during a procedure such as an angioplasty procedure, for example, and a tool, such as the guide wire used for such a procedure, for example, may be conveniently positioned within this channel to prevent the guide wire from being accidentally placed in contact with a non-sterile surface such as the floor.

As discussed above, a cover, such as drape 40, for example, can be pulled off the tray 20 after it has been used. In some instances, the drape 40 can be configured such that it can be inverted as it is removed from the tray 20. In one form, the drape 40 can include an open end that can be moved relative to body of the drape 40 such that an inner facing surface of the drape 40 becomes an outwardly facing surface and, correspondingly, an outwardly facing surface of the drape 40 becomes an inwardly facing surface. Once inverted, the seal 41, for example, could be utilized to re-seal the opening of the drape 40 with the drape 40 in its inverted position. Such an embodiment can allow the outer contaminated surfaces of the drape 40, and/or the items positioned thereon, to be captured within the drape 40. Once inverted and sealed, the drape 40 may encapsulate a significant quantity of air, for example. To remove the air from the inverted drape 40, a valve in the drape 40 could be utilized to remove the air. As the reader will recall, the drape 40 can include a valve 50 to remove the air from the interior cavity of the drape 40. To the extent that the valve 50 comprises a one-way valve, an additional valve in the drape 40 could be utilized to remove the air from the inverted drape 40. To the extent that the valve 50 comprises a two-way valve, the valve 50 could also be utilized to remove air from the inverted drape 40.

Figure 13:
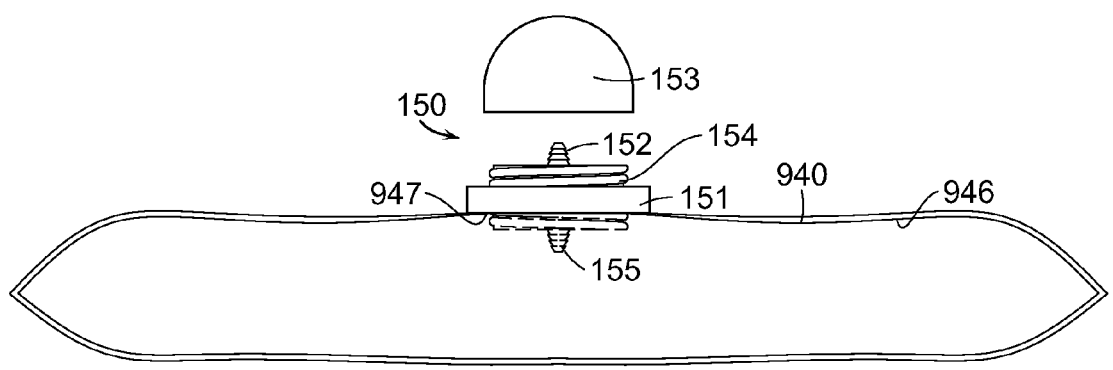
FIG. 13 is a cross-sectional view of a surgical drape including a valve in accordance with at least one embodiment.
Figure 14:
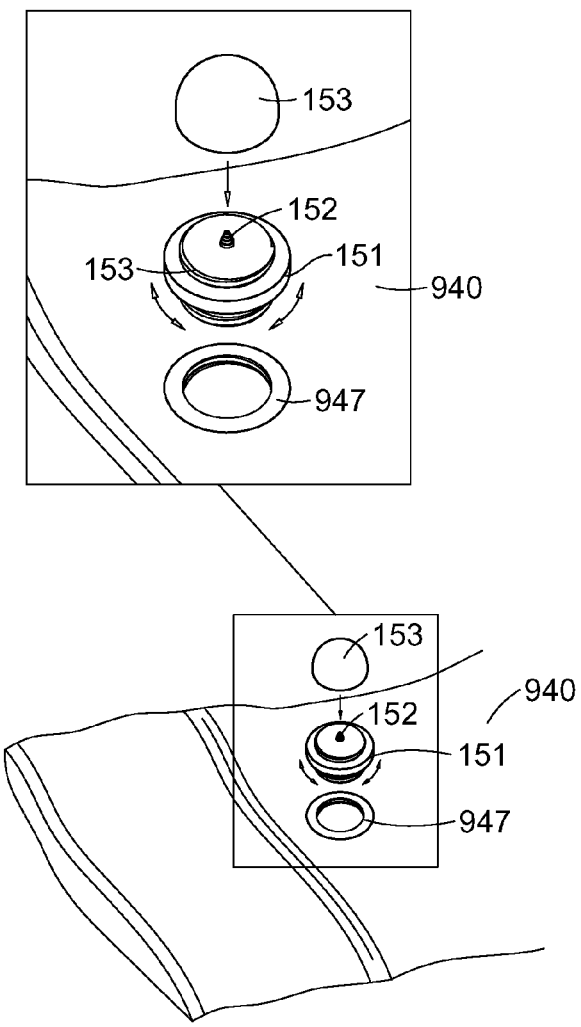
FIG. 14 is an exploded detail view of the valve of FIG. 13.

Further to the above, an embodiment of a drape, such as drape 940, for example, including a two-way valve 150 is illustrated in FIGS. 13 and 14. The two-way valve 150 can comprise a valve body 151 mounted to a valve opening 947 defined in the drape 940. In certain circumstances, the valve opening 947 can comprise a ring including a threaded aperture defined therein within which at least a portion of the valve body 151 can be positioned. In such circumstances, the outer surface of the valve body 151 can include threads which are configured to threadingly engage the threads defined in the valve opening 947. In some circumstances, the threaded interface between the valve opening 947 and the valve body 151 can comprise a seal. In at least one such circumstance, pipe threads and/or TEFLON PTFE tape, for example, can be utilized to create a seal at the threaded interface between the valve opening 947 and the valve body 151. In any event, the valve 150 can include a first valve element 152 which can be selectively attached to a vacuum source and permit air to be suctioned out of the interior cavity 946 of the drape 940 when a tray, for example, is positioned within the drape 940 in its uninverted condition. In the uninverted condition of the drape 940, the first valve element 152 faces outwardly while a second valve element 155 of the valve 150 faces inwardly. When the drape 947 is moved into its inverted condition, the second valve element 155 of the valve 150 may face outwardly while the first valve element 152 may face inwardly. In such circumstances, the second valve element 155 can be attached to a vacuum source and permit air to be suctioned out of the inverted and sealed drape 940. In various embodiments, the valve body 151 can include a threaded portion 154 which can permit a valve cover 153 to be attached to the valve body 151 when the valve element 152 is not attached to a vacuum source. In such circumstances, the valve cover 153 can protect the valve element 152. In certain embodiments, the valve body 151 can include a second threaded portion which can be configured to permit the valve cover 153 to be assembled to the valve body 151 to protect the second valve element 155 when the drape 940 is in its inverted condition, for instance.

In various instances, further to the above, the valve 50 and/or the valve 150, for example, can be removably mounted to a drape. In certain instances, a drape, such as drape 40, for example, can include a valve opening wherein a valve can be placed in fluid communication with the interior cavity of the drape through the valve opening. In various instances, the valve opening can comprise a closable aperture. In at least one such instance, the valve opening can comprise a seal which can include a first sealed, or substantially sealed, configuration in which a valve is not positioned in the valve opening and a second sealed, or substantially sealed, configuration in which the valve opening is sealed, or substantially sealed, against a valve positioned within the valve opening. Thus, in such embodiments, a valve could be selectively assembled to the valve opening to suction air from the drape when the drape is in its uninverted condition, removed, and then later reassembled to the opposite side of the valve opening when the drape is in its inverted condition.

Figure 12:
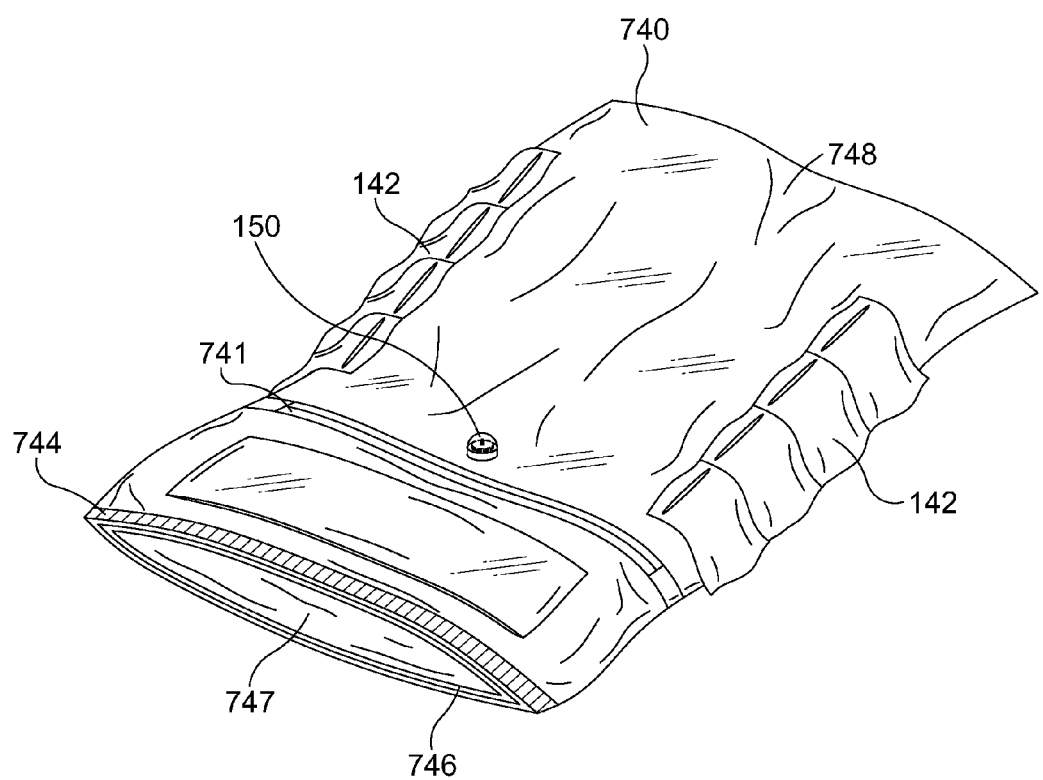
FIG. 12 is a perspective view of a surgical drape in accordance with at least one embodiment.
Figure 15:
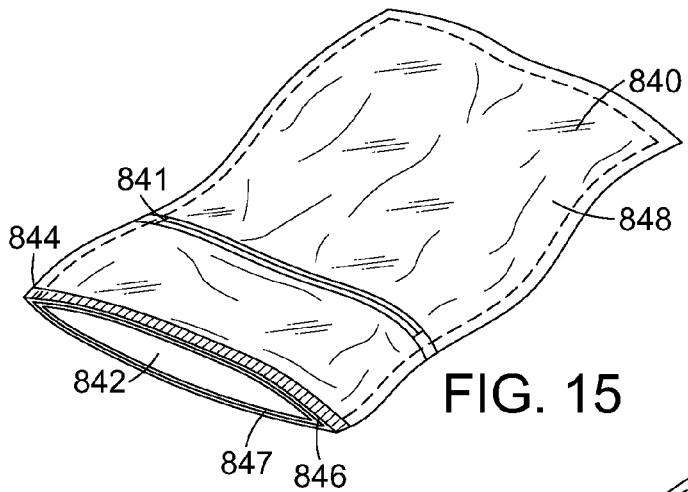
FIG. 15 is a perspective view of a surgical drape in accordance with at least one embodiment.
Figure 16:
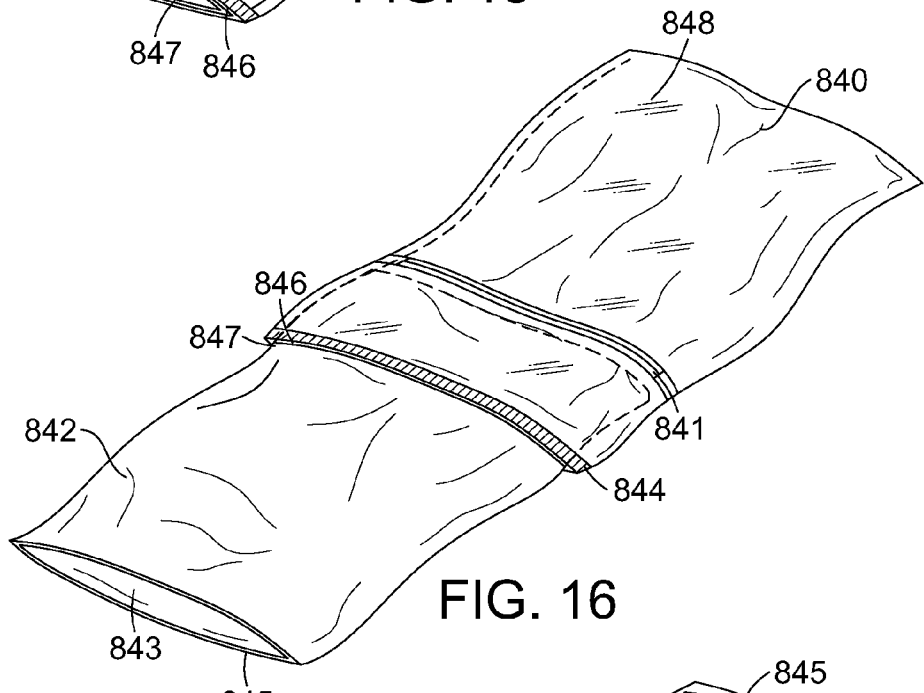
FIG. 16 is a perspective view of the surgical drape of FIG. 15 in an extended configuration.
Figure 17:
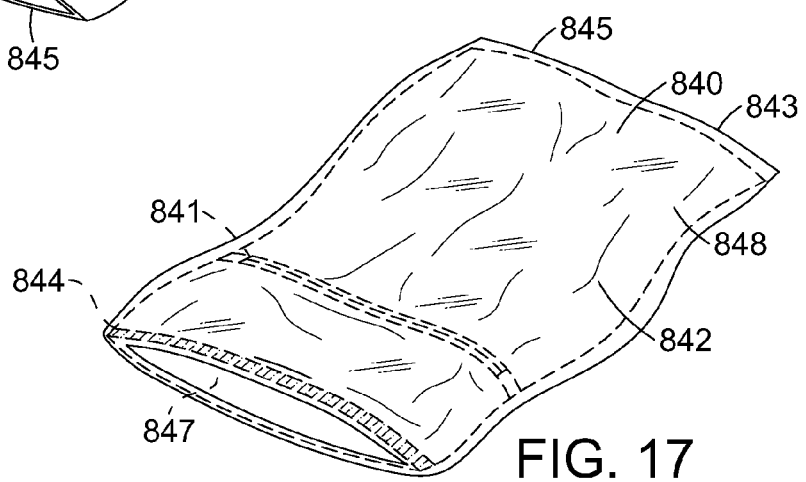
FIG. 17 is a perspective view of the surgical drape of FIG. 15 in an inverted configuration.

Further to the above, referring now to FIG. 12, a cover, such as a drape 740, for example, can include a first portion 748 including an interior cavity which can be sealingly enclosed by a seal 741. The drape 740 can further include a second portion 744 extending from the seal 741. The second portion 744 can include an opening 747 and a seal 746 configured to sealingly close the opening 747. In use, a tray can be inserted through the opening 747 and through the second portion 744 to position the tray within the interior cavity of the first portion 748. After the drape 740 has been used, the second portion 744 can be inverted to enclose, or at least partially enclose, the first portion 748 of the drape 740. Once the first portion 748 is positioned within the second portion 744, the first portion 748 can be sealed within the second portion 744 utilizing the seal 746, for instance. Turning now to FIGS. 15-17, a cover, such as a drape 840, for example, can include a first portion 848 including an interior cavity which can be sealingly enclosed by a seal 841. The drape 840 can further include a second portion 844 extending from the seal 841. The second portion 844 can include an opening 847 and a seal 846 configured to sealingly enclose the opening 847. In use, a tray can be inserted through the opening 847 and through the second portion 844 to position the tray within the interior cavity of the first portion 848. The drape 840 can further include an extendable portion 842 removably positioned within the second portion 844. Similar to the second portion 844, the extendable portion 842 can include an opening 843 through which the tray can be inserted to position the tray in the first portion 848. In at least one such embodiment, the extendable portion 842 can be affixed the second portion 844. After the drape 840 has been used, the extendable portion 842 can be pulled out of the second portion 844 and then inverted to enclose, or at least partially enclose, the first portion 848 and the second portion 844 of the drape 840. Once the first portion 848 and the second portion 844 are positioned within the extended portion 842, the first portion 848 and the second portion 844 can be sealed within the extended portion 842 utilizing a seal 845, for instance.

Figure 5:
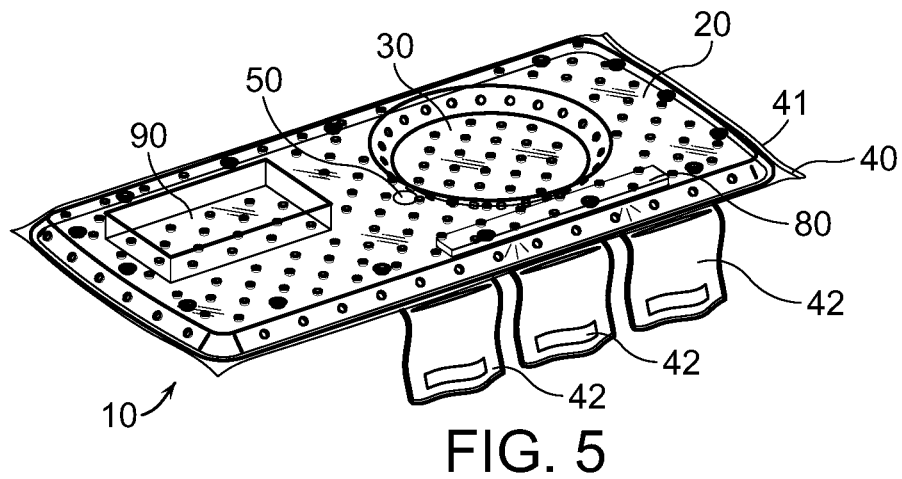
FIG. 5 is a perspective view of another surgical tray system in accordance with at least one embodiment.
Figure 6:
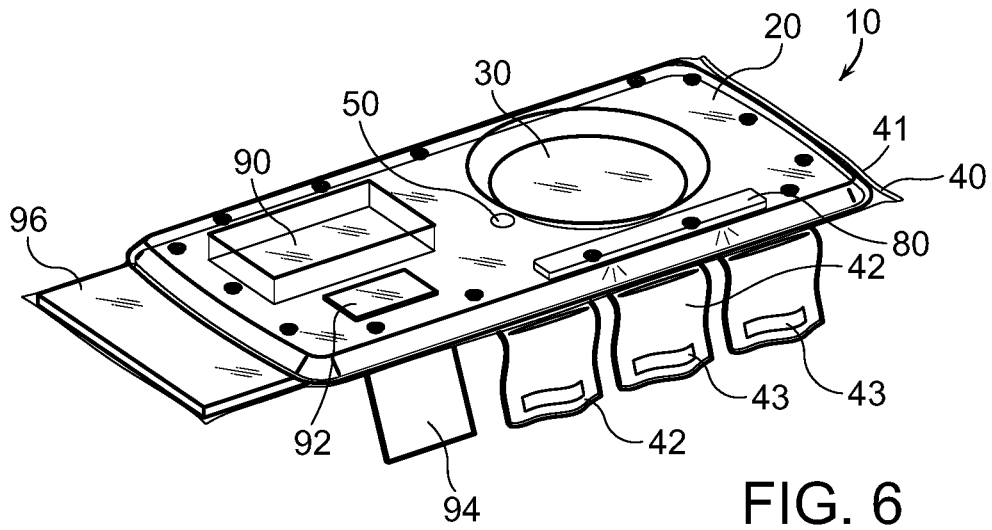
FIG. 6 is a perspective view of another surgical tray system in accordance with at least one embodiment.

In various embodiments, turning now to FIGS. 5 and 6, a cover, such as drape 40, for example, can include one or more external pouches 42 attached to the drape 40. In at least one such instance, the external pouches 42 may be heat-welded to the drape 40. In certain instances, at least one adhesive, hooks, hook and loop fasteners, and/or any other suitable attachment elements or methods could be utilized. In certain embodiments, the external pouches 42 can be integrally formed with the drape 40. The pouches 42 can provide one or more storage areas. In certain instances, the pouches 42 can include labels 43. Drapes including pouches 142 are depicted in FIGS. 8-12. A surgical instrument system 510 is depicted in FIGS. 23-26 which utilizes a large pouch 542.

As discussed above, a tray, such as tray 120, for example, can include a first support 322 and a second support 424 extending therefrom. In various instances, the first support 322 and/or the second support 424 can comprise modular components which can be selectively assembled to the tray 120. In certain instances, the first support 322 and/or the second support 424 can include an expandable portion 515 wherein each expandable portion, in some circumstances, can include an accordion type configuration. Moreover, any portions of the surgical tray assemblies discussed herein can comprise modular components which can be assembled together. For instance, a clinician can select modular tray portions from a kit including a modular portion comprising a window, a modular portion comprising a light, a modular portion comprising a bowl-shaped indentation, a modular portion comprising a magnification element, a modular portion comprising a trough, a modular portion comprising a support, and/or a modular portion comprising an attachment portion, for example, and assemble the selected portions together. In such instances, each modular portion could include a universal connection system which could permit any two or more modular portions to be assembled together.

As discussed herein, methods for covering a surgical room object are disclosed herein. Certain methods include the step of enveloping an object in a drape cover adapted to conform to the object. Such a step can include fully encapsulating an object, or alternatively, enveloping an object so that the drape cover may be sealed or substantially sealed about a portion of the object. Various methods further include the step of sealing or substantially sealing the drape cover around or about the object. Furthermore, various methods include the step of suctioning air out of an interior area of the drape cover to create a close conformity between the drape cover and the object. In some embodiments, suctioning the air out of the drape cover causes the drape cover to conform closely to at least one indentation in the tray, table, or object. In various embodiments, air can be suctioned out of the drape cover in a first step and then sufficiently sealed in a second step so that a vacuum is maintained, or at least substantially maintained, within the drape cover. Alternatively, a vacuum within a drape cover can be maintained by continuously suctioning air out of the drape cover during use. Certain methods can include the step of suctioning air through an opening in a support arm extending through the drape cover opening. Various methods can include the step of positioning a valve within a valve opening in the drape cover and/or removing the valve from the valve opening after the valve has been used. Certain methods can include the step of positioning a valve opening and/or valve in the drape cover to coincide with the position of an opening in the object which is in communication with at least one vent in the object and suctioning air out of the object through the opening in the object via the valve opening and/or valve in the drape cover.

Various methods further include the steps of unsealing the drape cover after it has been used, removing the drape cover from the object, and/or inverting the drape cover. Certain methods further include the step of sealing the drape cover after the step of inverting the drape cover. Methods disclosed herein can also include the step of suctioning air or fluids out of the drape cover via a valve opening in the drape cover after the step of sealing the drape cover. In various embodiments, indicia may be present on the drape cover to assist a clinician in performing any of the steps identified herein. For example, directional indicators to help instruct the clinician as to how to deploy the drape cover about an object may be included, as well as indicators that can be matched to certain portions of the object so that the clinician can discern whether the drape cover is fully deployed.

In various instances, a system disclosed herein can comprise a floor-mounted, bed-mounted, and/or ceiling-mounted system, for example, that can include one or more ergonomic surfaces. In certain instances, the system can include a pre-modeled base-platform and/or a modular system allowing for a plurality of items to be attached to a base-platform. In at least one instance, the base-platform, or at least portions of the base-platform, can be comprised of a polycarbonate, an acrylic, and/or a poly(methyl methacrylate) such as LUCITE, for example, material which can also include a LED contained and/or impregnated within the base-platform. In various instances, the base-platform, such as a tray and/or table, for example, could act as an ergonomic surface and/or a shield for radiation scatter within the applicable procedural environment. In various instances, the system can include a correlating or matching sterile vacuum form-fitted covering that can cover the one or more ergonomic surfaces of an object within a procedural environment. Such a covering can increase and/or maximize the sterile surface area of a non-sterile object enclosed within. In various instances, as outlined above, the air pressure within the covering can be less than the air pressure surrounding the covering and, owing to this pressure differential, the covering can be pushed inwardly toward the object so long as a pressure differential is maintained. In the event that the covering is ruptured and/or a pressure differential is not maintained, the covering may no longer be vacuum-fitted to the object which may provide a visual indicator to a clinician that a breach in the cover may exist. After the system has been used during a procedure, the once sterile-covering can be inverted as it is removed from the object and/or ergonomic surface in order to enclose and/or encapsulate the procedural waste and/or pathogens that were placed on the covering during the procedure.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical tray system, comprising:
   a surgical tray having an air flow aperture in fluid communication with an upper surface and a lower surface of said surgical tray; and
   a vacuum-fitted cover covering at least a portion of said surgical tray, said vacuum-fitted cover comprising:
   a flexible material that defines an interior cavity of the vacuum-fitted cover, the vacuum-fitted cover including an opening, the opening and the interior cavity sized to permit the surgical tray and an attached support device to be inserted through the opening and situated at least partly within the interior cavity;
   a valve in fluid communication with said interior cavity, said valve configured to enable suction of air from said interior cavity and to draw said flexible material inwardly toward a surface of said surgical tray, and further configured to be aligned with the air flow aperture; and a seal arrangement that enables (a) the vacuum-fitted cover to be sealed in a non-inverted condition with the surgical tray in the interior cavity, and (b) the vacuum-fitted cover to be sealed in an inverted condition in which the interior cavity is outward facing.

2. The surgical tray system of claim 1, wherein said surgical tray is configured to be supported by a floor-supportable stand.

3. The surgical tray system of claim 1, wherein said attached support device includes or is attached to at least a movable arm, wherein said surgical tray is mounted to said movable arm.

4. The surgical tray system of claim 1, further comprising at least one light mounted to said surgical tray, wherein said at least one light is configured to illuminate a surgical site located underneath the lower surface of said surgical tray.

5. The surgical tray system of claim 1, further comprising at least one light emitting diode mounted relative to the lower surface of said surgical tray, wherein said vacuum-fitted cover covers said lower surface and said at least one light emitting diode.

6. The surgical tray system of claim 1, wherein said surgical tray comprises a first modular component and a second modular component.

7. The surgical tray system of claim 6, wherein said first modular component and said second modular component are selected from a plurality of modular components.

8. The surgical tray system of claim 1, wherein said surgical tray is comprised of a material sufficiently transparent to permit a clinician to view a surgical site through said surgical tray.

9. The surgical tray system of claim 8, wherein said vacuum-fitted cover is comprised of a material sufficiently transparent to permit a clinician to view the surgical site through said surgical tray and said vacuum-fitted cover.

10. The surgical tray system of claim 1, wherein said surgical tray is comprised of a translucent material.

11. The surgical tray system of claim 10, wherein said vacuum-fitted cover is comprised of a translucent material.

12. The surgical tray system of claim 1, wherein said surgical tray further comprises an indentation formed in the upper surface of said surgical tray, and wherein said vacuum-fitted cover is form-fitted into said indentation.

13. The surgical tray system of claim 1, wherein said valve comprises a one-way valve that permits air to be suctioned through said valve in a first direction and that prohibits airflow in a direction opposite to said first direction.

14. The surgical tray system of claim 1, wherein said valve comprises a two-way valve including a first opening and a second opening, wherein said two-way valve is configured to permit air to be suctioned through said two-way valve in a first direction by a vacuum source applied to said first opening, wherein said two-way valve is configured to permit air to be suctioned through said two-way valve in a second direction by the vacuum source or another vacuum source applied to said second opening, and wherein said two-way valve is in a closed condition when a vacuum source is not applied to said first opening or said second opening thereby prohibiting airflow.

15. The surgical tray system of claim 1, wherein said surgical tray further comprises a magnification element.

16. The surgical tray system of claim 1, wherein said vacuum-fitted cover comprises a magnification element.

17. The surgical tray system of claim 1, wherein said vacuum-fitted cover comprises at least one pocket.

18. A surgical drape, comprising:
an interior cavity configured to receive a surgical tray and a support device attached to the surgical tray, wherein said interior cavity is defined by a flexible wall;
an opening;
a seal arrangement configured to (a) close said opening and enclose at least a portion of the support device within said interior cavity, and (b) seal the surgical drape-in an inverted condition in which the interior cavity is outward facing; and
a valve arrangement in fluid communication with said interior cavity, said valve arrangement configured to enable suction of air from said interior cavity and to draw said flexible wall inwardly toward a surface of the surgical tray, and further configured to be aligned with an air flow aperture of the surgical tray.

19. A surgical drape comprising:
a flexible material that defines an interior cavity of the surgical drape, the surgical drape including an opening, the opening and the interior cavity sized to permit a surgical tray and an attached support device to be inserted through the opening and situated at least partly within the interior cavity; and
a valve arrangement in fluid communication with said interior cavity, said valve arrangement configured to enable suction of air from said interior cavity and to draw said flexible material inwardly toward a surface of said surgical tray, and further configured to be aligned with an air flow aperture of the surgical tray.

20. The surgical drape of claim 19, further comprising a seal arrangement that enables (a) the surgical drape to be sealed in a non-inverted condition with the surgical tray placed into the interior cavity, and (b) the surgical drape to be sealed in an inverted condition in which the interior cavity is outward facing, wherein the seal arrangement includes a first seal element configured to seal the surgical drape in the non-inverted condition and a second seal element configured to seal the surgical drape in the inverted condition.

21. The surgical drape of claim 20, wherein the flexible material includes a first portion configured to house the surgical tray and a second portion configured to be inverted and to contain the first portion while the surgical drape is in the inverted condition.

22. The surgical drape of claim 20, wherein:
the seal arrangement further includes a third seal element configured to seal the surgical drape in the inverted condition;
the flexible material includes a first portion, a second portion, and a third portion, the first portion configured to house the surgical tray in the non-inverted condition, and the third portion includes the opening of the surgical drape;
the first seal element is situated between the first portion and the second portion, and the second seal element is situated between the second portion and the third portion; and
the third portion is configured to be inverted and to contain the first portion and the second portion while the surgical drape is in the inverted condition.

23. The surgical drape of claim 19, further comprising a seal arrangement, wherein the seal arrangement includes a seal element that is configured to seal the surgical drape in a non-inverted condition or in an inverted condition.

24. The surgical drape of claim 19, further comprising a seal arrangement, wherein the seal arrangement is configured to form a seal around the attached support device.

25. The surgical drape of claim 19, wherein the valve arrangement includes a two-way valve.

26. The surgical drape of claim 19, wherein the valve arrangement includes a one-way valve configured to permit airflow from the interior cavity to an exterior of the surgical drape.

27. The surgical drape of claim 26, wherein the one-way valve is a first one-way valve to permit airflow in a first direction relative to the interior cavity, and the valve arrangement further includes a second one-way valve configured to permit airflow in a second direction opposite to the first direction.

28. The surgical drape of claim 19, wherein the valve arrangement includes a valve opening configured to accept a valve removably assembled in a first position such that the valve permits airflow in a first direction relative to the interior cavity, and a second position such that the valve permits airflow in a second direction opposite to the first direction.

29. The surgical drape of claim 19, further comprising a seal arrangement that enables (a) the surgical drape to be sealed in a non-inverted condition with the surgical tray placed into the interior cavity, and (b) the surgical drape to be sealed in an inverted condition in which the interior cavity is outward facing.

* * * * *